United States Patent
Gagliardi et al.

Patent Number: 5,468,771
Date of Patent: Nov. 21, 1995

[54] CHOLESTEROL LOWERING COMPOUND

[75] Inventors: Magda M. Gagliardi, Somerset; Shieh-Shung T. Chen, Morganville; Byron H. Arison, Watchung; George M. Garrity, Westfield; Leeyuan Huang, Watchung; John G. MacConnell, Westfield, all of N.J.; Raymond F. White, Palmyia, Va.

[73] Assignee: Merck & Co., Inc., Rahway, N.J.

[21] Appl. No.: 190,110

[22] PCT Filed: Aug. 5, 1992

[86] PCT No.: PCT/US92/06520

§ 371 Date: Feb. 2, 1994

§ 371 Date: Feb. 2, 1994

[87] PCT Pub. No.: WO93/03038

PCT Pub. Date: Feb. 18, 1993

Related U.S. Application Data

[63] Continuation of Ser. No. 741,699, Aug. 7, 1991, abandoned.

[51] Int. Cl.⁶ ........................ A61K 31/35; C07D 319/04
[52] U.S. Cl. ............................................. 514/452; 549/363
[58] Field of Search ............................. 549/363; 514/452

[56] References Cited

U.S. PATENT DOCUMENTS

| | | |
|---|---|---|
| 5,026,554 | 6/1991 | Bartizal et al. |
| 5,096,923 | 3/1992 | Bergstrom et al. |
| 5,256,689 | 10/1993 | Chiang et al. |
| 5,258,401 | 11/1993 | Berger et al. |
| 5,270,332 | 12/1993 | Chen et al. |
| 5,284,758 | 2/1994 | Bills et al. |

FOREIGN PATENT DOCUMENTS

| | | |
|---|---|---|
| 0450812 | 10/1991 | European Pat. Off. |
| 0512865 | 11/1992 | European Pat. Off. |
| 0524677 | 1/1993 | European Pat. Off. |
| 92/12159 | 7/1992 | WIPO |
| 92/12158 | 7/1992 | WIPO |
| 92/12160 | 7/1992 | WIPO |
| 92/12156 | 7/1992 | WIPO |
| 93/18039 | 9/1993 | WIPO |
| 93/18040 | 9/1993 | WIPO |
| 93/17557 | 9/1993 | WIPO |

*Primary Examiner*—Nicky Chan
*Attorney, Agent, or Firm*—Carol S. Quagliato; Melvin Winokur

[57] ABSTRACT

A compound of structural formula

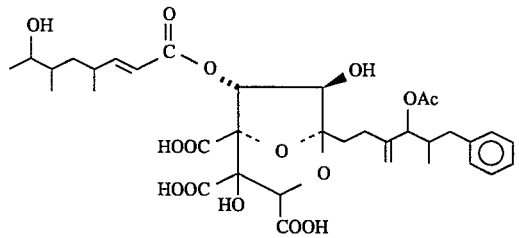

having antihypercholesterolemic utility is produced by culturing a Streptomyces sp. in a nutrient medium in the presence of a substrate of structural formula:

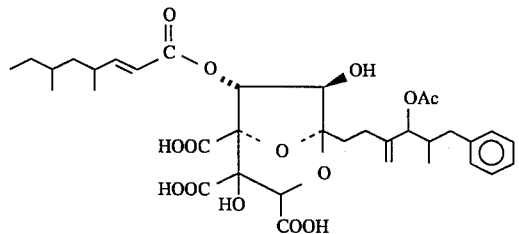

5 Claims, No Drawings

CHOLESTEROL LOWERING COMPOUND

This application is a 371 of PCT/US92/06520 filed Aug. 5, 1992, which itself was a continuation of U.S. Ser. No. 07/741,699 filed Aug. 7, 1991 (now abandoned).

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analogs containing compounds such as those described in P. Oritz de Montellano et al., J. Med Chem. 20, 243 (1977) and E. J. Corey and R. Volante, J, Am. Chem. Soc., 98, 1291 (1976). S. Billet (U.S. Pat. No. 4,871,721) described isoprenoid (phosphinylmethyl)phosphonates as inhibitors of squalene synthetase.

Recently certain nonphosphorus containing inhibitors of squalene synthetase have been isolated as natural products. These natural product inhibitors are described in U.S. Pat. Nos. 5,132,320 issued Jul. 21, 1992, 5,096,923 issued Mar. 17, 1992 and 5,102,907 issued Apr. 7, 1992. A need still remains for a more effective squalene synthetase inhibitor, i.e. one that provides a greater antihypercholesterolemic effect and exhibits a good safety profile.

The present invention is directed to a biotransormed analog of the above-noted natural products.

DETAILED DESCRIPTION OF THE INVENTION

This invention is concerned with a compound of structural formula (I) which is useful as a cholesterol lowering agent:

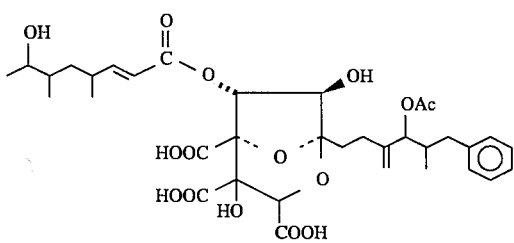

or a pharmaceutically acceptable salt thereof. Chemically this compound is known as (1S,3S,4S,5S,6R,7R)-1-[(4S)-acetoxy-3-methylene-5-methyl-6-phenyl] hexyl-4,6,7-trihydroxy-6-0-(4,6-dimethyl-7-hydroxy-2-octenoyl)-2,8-dioxabicyclo [3.2.1]octane-3,4,5-tricarboxylic acid.

The compound of structural formula I is prepared by biotransformation of the compound of structural formula II:

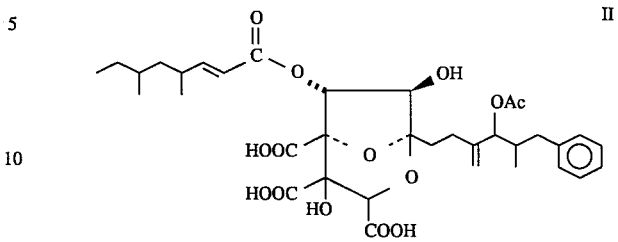

by incubation of a Streptomyces sp., in a nutrient medium in the presence of the compound of structural formula II.

The preferred strain of the Streptomyces sp. is believed to be *Streptomyces cyanus* and is deposited in the culture collection of Merck & Co. Inc., Rahway, N.J. as HA 6962. A sample of this was deposited Jul. 24, 1991 under the Budapest Treaty with the American Type Culture Collection at 1230, Parklawn Drive, Rockville Md. 20852 and has been assigned accession number ATCC 55214.

The following is a general description of Streptomyces sp., strain HA6962, ATCC 55214.

Observations of growth, general cultural characteristics and carbon source utilization were made in accordance with the methods of Shitling and Gottleib (Internat. J. System. Bacteriol. 16: 313–340). Chemical composition of the cells was determined using the methods of Lechevalier and Lechevalier (in Actinomycete Taxonomy, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985).

Source

This culture was isolated from a soil sample collected in Somerset, NJ.

Analysis of Cell Wall Composition:

Peptidoglycan contains LL-diaminopimelic acid.

General Growth Characteristics:

Good growth on yeast malt extract agar (YME), glycerol asparagine agar, inorganic salt starch agar, oatmeal, trypticase soy agar, Czapek's agar, and peptone iron agar. Fair growth on tap water agar supplemented with NZ-amine (Shefield Chemical Co.). Culture also grows in tryprone yeast extract broth. Culture grows at 27° C. and 37° C..

Colony morphology- (on YME at 21 d):

Substrate mycelium is medium brown. Aerial mycelium white. Spore mass is abundant and light brownish gray in color. Colonies are opaque, raised and have entire edges, rubbery in consistency with a rough surface texture.

Micromorphology:

Aerial mycelia (0.57 μm) arise from substrate mycelia and are branched and slightly flexous. In mature cultures (7–28d p.i.) the aerial mycelium terminates in flexous chains of spores that occasionally terminate in hooks, loops or open spirals. This characteristic is especially noticeable in areas of dense aerial development. Sporulation occurs on YME, inorganic salts-starch agar, oatmeal, glycerol asparagine agar, tap water agar with NZ-amine and Czapek's agar. On oatmeal agar knot-like structures are observed at the junction of hyphae.

Miscellaneous physiological reactions:

Culture produces $H_2S$ in peptone-iron agar. Melanoid pigments are formed in TY broth and on peptone iron agar slants. Starch is weakly hydrolyzed. Carbon source utilization pattern is as follows: good utilization of L-arabinose, cellobiose, D-fructose, α-D-glucose, inositol, α-D-lactose, β-D-lactose, D-maltose, D-mannitol, D-mannose, D-raffinose, L-rhamnose, sucrose, D-xylose; moderate utilization of D-arabinose, no utilization of L-xylose.

Diagnosis:

Cell wall analysis reveals that MA 6962 has a type I cell wall. Morphological studies reveal that the culture produces long chains of spores on spiral sporophores that terminate in loops, hooks or extended spirals. Sporophores arise from the aerial mycelium. These are characteristics typica, for strains of Streptomyces. A comparison of the phenotypic data of MA 6962 with that of the validly published species of Streptomyces in the taxonomic literature (1–7) shows that this strain bears a resemblance to *Streptomyces bottropensis* and *Streptomyces resistomycificus*. The former is currently considered aligned species of *Streptomyces diastaticus* and the latter is a subjective synonym of *Streptomyces cyanus*. Both of these species characteristically produce spores on sporophores that terminate in loops, hooks or spirals, both produce melanoid pigments and both exhibit similar carbon source utilization patterns. There are, however some differences. Neither of these species were reported to form knot-like structures in the aerial hyphae as was observed in cultures of MA 6962. Furthermore, *Streptomyces bottropensis* is noted for the production of short chains of large diameter spores on both the aerial and vegetative mycelia. We did not observe such spores in cultures of MA 6962. Based on these data, it is believed that MA 6962 is a novel strain of *Streptomyces cyanus*.

1. Shitling, E. B. and Gottlieb, D., Int. J. System. Bacteriol. 18:69 (1968).

2. Shitling, E. B. and Gottlieb, D., Int. 3. System. Bacteriol. 18:279 (1968).

3. Shitling, E. B. and Gottlieb, D., Int. J. System. Bacteriol. 19:391 (1969).

4. Shitling, E. B. and Gottlieb, D., Int. J. System. Bacteriol. 22:265 (1972).

5. Nonomura, H. J. Ferment. Technol. 52:78 (1974).

6. Pridham, T. and Tresner, H., in Bergey's Manual of Determinative Bacteriology, Eight Edition, R. E. Buchanan and N. E. Gibbons, Ed., Williams and Wilkins, Baltimore (1974).

7. Loci, R. in Bergey's Manual of Systematic Bacteriology, Vol. 4., St. Williams, M. E. Sharpe and J. G. Holt. Ed., Williams and Wilkins, Baltimore. (1989).

| Cultural Characteristics of Streptomyces sp. MA 6962 at 21 days | | | | |
|---|---|---|---|---|
| Medium | Amount of Growth | Aerial Mycelium and/or Spores | Soluble Pigments | Reverse Color |
| Yeast Extract Malt Extract | good | Aerial mycelium light brownish gray (63 l. brGray). Spores borne in slightly flexous chains with terminal hooks, loops and extended spirals. | none noted | Medium brown (58 m. Br) |
| Glucose Asparagine | good | Aerial mycelium light brownish gray (63 l. brGray). Spores borne in slightly flexous chains with terminal hooks, loops and extended spirals. | none noted | Medium brown (58 m. Br) |
| Inorganic Salts | good | Aerial mycelium light gray (264 l. Gray). Spores borne in slightly flexous chains with terminal hooks, loops and extended spirals. Starch weakly hydrolyzed. | none noted | Light gray yellow-brown (79 l. gy. YBr) |
| Oatmeal | good | Aerial mycelium light gray (264 l. Gray) to light brownish gray (63 l. brGray) Spores borne in slightly flexous chains with terminal hooks, loops and extended spirals. Knot-like structures in aerial hyphae. | none noted | light gray brown (60 l. gy. Br) |
| Tap Water | sparse | Transparent. Sproes borne in long, open spirals. | none noted | Transparent |
| Czapek | good | White (263 White) to grayish yellow brown (80 gy. YBr) Poorly developed. Spores borne in short spirals and hooks. | none noted | Grayish brown (80 gy. yBr) |
| Peptone Iron | good | | Melanin positive, $H_2S$ positive. | |

| Carbohydrate Utilization Pattern of Streptomyces sp. MA 6962 at 21 Days | |
|---|---|
| Carbon Source | Utilization |
| D-arabinose | 1 |
| L-arabinose | 3 |
| cellobiose | 3 |
| D-fructose | 3 |
| inositol | 3 |
| α-D-lactose | 3 |
| β-D-lactose | 3 |
| D-maltose | 3 |
| D-mannitol | 3 |
| D-mannose | 3 |
| D-raffinose | 3 |
| L-rhamnose | 3 |
| sucrose | 3 |
| D-xylose | 3 |
| L-xylose | 0 |
| α-D-glucose (control) | 3 |

3 = good utilization
2 = moderate utilization
1 = poor utilization
0 = no-utilization Compound I is produced during the aerobic fermentation of a suitable aqueous nutrient media in the presence of Compound II under conditions described hereinafter, with a producing strain of the Streptomyces Such nutrient media contain sources of carbon and nitrogen assimilable by the microorganism and generally low levels of inorganic salts. In addition, the fermentation media may contain traces of metals necessary for the growth of the microorganisms. These are usually present in sufficient concentration in the complex sources of carbon and nitrogen which may be used as nutrient sources, but can, of course, be added separately to the medium if desired.

In general, carbohydrates such as sugars, for example dextrose, maltose, lactose, dextran, cerelose and the like, and starches are suitable sources of assimilable carbon in the nutrient media. The exact quantity of the carbon source which is utilized in the medium will depend, in part, upon the other ingredients in the medium but it is usually found that an amount of carbohydrate between about 0.5 and 5% by weight of the medium is satisfactory. These carbon sources can be used individually or several such carbon sources may be combined in the same medium.

Various nitrogen sources such as yeast hydrolysates, yeast autoysate, soybean meal, casein hydrolysates, yeast extracts, corn steep liquors, distillers solubles, cottonseed meal, meat extract and the like, are readily assimilable by the Streptomyces sp. in the production of Compound I. The various sources of nitrogen can be used alone or in combination in amounts ranging from about 0.2 to 6% by weight of the medium.

Among the nutrient inorganic salts which can be incorporated in the culture media are the customary salts capable of yielding sodium potassium, magnesium, ammonium, calcium, phosphate, sulfate, chloride, carbonate and like ions. Also included are trace metals such as cobalt, manganese, iron and the like.

It should be noted that the media described hereinbelow and in the Examples are merely illustrative of the wide variety of media which may be employed, and are not intended to be limitative.

EXAMPLE 1

Preparation (1S,3S,4S,SR,6R,7R)-1-[(4S)-acetoxy-3-methylene-5-methyl- 6-phenyl]hexyl-4,6,7-trihydroxy-6-O-(4, 6-dimethyl-7-hydroxy-2-octenoyl)T2,8-dioxabicyclo[ 3.2.1]-octane-3.4.5-tricarboxylic acid Step A: Preparation of (1S,3S,4S,5R,6R,7R)-1-[(4S)-acetoxy-3-methylene- 5-methyl-6-phenyl]-hexyl-4,6,7-trihydroxy-6-O-(4,6-dimethyl-2-octenoyl)-2, S-dioxabicyclo[3.2.1]octane-3,4-5-tricarboxylic acid 1. Culturing MF5453

Culture MF5453 (ATCC 20986) was inoculated into KF seed medium using one glass scoop of the original soil tube. The KF seed flask was incubated for 73 hours at 25° C., 220 rpm, 85% humidity. At the end of this incubation, 2.0 mls aliquots were aseptically transferred to each of 75 MBM production medium flasks. These production flasks were then incubated at 25° C., 220 rpm, 85% humidity, with a fermentation cycle of 14 days. Flasks were harvested as follows: mycelial growth was homogenized for 20 seconds at high speed using Biohomogenizer/mixer (Biospec Products Inc. Bartlesville, Ok); and then 45 mls methanol was added to each flask (final methanol concentration was approximately 50%). Flasks were then returned to the shaker and agitated at 220 rpm for 30 minutes. Subsequently, the contents of the flasks were pooled.

2. Isolation of Compound (II)

A 6 liter 50% methanol homogenized fungal extract exhibiting a pH of 4.5 was employed in the following isolation procedure. The mycelia was filtered through celite and the recovered mycelia was extracted again by stirring overnight with 3 L of 50% methanol and again filtered.

The combined extract (9 L) of 50% methanol was diluted to 25% methanol with water (total volume 18 L) and applied to a Mitsubishi ]tP-20 column (750 ml) at a flow rate of 80 ml/minute. The column was washed with water (1 L) and eluted with a stepwise gradient of methanol consisting of 50/50 methanol/$H_2O$ (1 L), 60/40, methanol/$H_2O$ (1 L), 80/20 methanol/$H_2O$ (2 L,) 90/10 methanol/$H_2O$ (1 L), 100% methanol (2 L), and 100% acetone (1 L). The fractions from 50/50 to 90/10 methanol/$H_2O$ were combined and diluted with water to 35/65 methanol/$H_2O$ (total volume 10 L).

The 10 L of 35/65 methanol/$H_2O$ was acidified with 1.0 N HCl (20 ml) to pH 3.0 and extracted into EtOAc (4 L). The EtOAc layer was separated and the solvent removed in vacuo to yield 260 mg of an orange oil.

A portion (10%) of the orange oil was dissolved in 1 ml methanol and diluted with 0.8 ml 10 mM potassium phosphate (pH 6.5) with some precipitation. The suspension was applied to a preparative EPLC column (Whatman Magnum 20 $C_{18}$, 22 mm ID×25 cm, 8 ml/minute. The initial mobile phase was 60/40 methanol/10 mM $K_3PO_4$, pH 6.5, and after 20 minutes the mobile phase was changed to 80/20 methanol/10 mM potassium phosphate, pH 6.5. Fractions of 8 ml each were collected, and the fractions from 31 to 33 minutes were combined, diluted with water to 35% methanol, acidified with 10% HCl to pH 3, and extracted into EtOAc. The solvent was removed in vacuo and a clear slightly yellow oil identified as the titled compound was obtained.

| KF SEED MEDIUM | per liter |
|---|---|
| Corn Steep Liquor | 5 g |
| Tomato Paste | 40 g |
| Oat Flour | 10 g |
| Glucose | 10 g |
| Trace Element Mix | 10 ml |
| pH adjusted to 6.8 (presterile) | |

-continued 50 mls/nonbaffled 250 mls
Erlenmeyer flask
autoclave 20 minutes (121° C.,
15 psi)

| | g/L |
|---|---|
| Trace Elements Mix | |
| FeSO$_4$.7H$_2$O | 1.0 |
| MnSO$_4$.4H$_2$O | 1.0 |
| CuCl$_2$.2H$_2$O | 0.025 |
| CaCl$_2$.2H$_2$O | 0.1 |
| H$_3$BO$_3$ | 0.056 |
| (NH$_4$)$_6$Mo$_7$O$_{24}$.4H$_2$O | 0.019 |
| ZnSO$_4$.7H$_2$O | 0.2 |
| dissolved in 1 L 0.6 N HCl | |
| MBM Products Medium | |
| Malt extract (Difco) | 5.0 |
| Glucose | 15.0 |
| Peptone | 1.0 |
| KH$_2$PO$_4$ | 1.0 |
| MgSO$_4$ | 0.5 |
| distilled H$_2$O | 1000.0 mls |
| (no pH adjustment) | |
| 45 mls/nonbaffled 250 mls Erlenmeyer flask | |
| autoclave 15 minutes (121° C., 15 psi) | |

Step B: Preparation of (1S,3S,4S,5R,6R,7R)-1-[(4S)-acetoxy- 3-methylene-5-methyl-6-phenyl ]hexyl-4,6-7-trihydroxy-6-O-( 4,6-dimethyl-7-hydroxy-2-octenoyl )-2,8-dioxabicyclo[-3.2.1 ]octane-3.4,5-tricarboxylic acid (I)

1. Fermentation:

A frozen vial (2.0 mL) of culture MA 6962 was used to inoculate a 250 mL baffled shake flask containing 50 mL of medium A. The seed flask was incubated on a rotary shaker (220 rpm) at 27° C. for 24 hours. A 2.5 mL aliquot of the developed seed was used to inoculate a 250 mL non-baffled flask containing 50 mL of Soy-glucose medium. Product from Step A was added to the fermentation at 24 hours to achieve a final concentration of 0.05 mg/mL. The shake flask contents were subsequently incubated at 27° C. on a rotary shaker for 4 days. The resultant whole broth was extracted as described in Part 2.

| Media: | |
|---|---|
| | g/L |
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| MgSO$_4$.7H$_2$O | 0.05 |
| K$_2$HPO$_4$ | 0.3 |
| Adjust pH to 7.1 | |
| Add CaCO$_3$ | 0.5 |
| Soy-Glucose Medium | |
| Glucose | 20.0 |
| Soya Meal | 5.0 |
| Yeast Autolysate | 5.0 |
| NaCl | 5.0 |
| MES | 9.8 |
| Adjust pH to 7.0 | |

2. Isolation and Purification:

To about 1.5 L of whole borth originally containing 75 mg of product from Step A as substrate, was added an equal volume of methanol; this was left on the lab bench overnight. The cellular debris was removed by centrifugation and the methanol was removed on the rotary evaporator. The pH was adjusted to about 2.5 with phosphoric acid and the dark brown fluid was extracted with ethyl acetate. Water was added and the ethyl acetate was removed on the rotary evaporator. This liguid (250 mY.) was passed through a HP-20 resin column (2×21 cm). Fractions (200 mL) were collected as the methanol concentration of the eluant was changed in 10% increments. Fractions were monitored by HPLC and those containing the metabolites of interest were pooled. This material was purified by passage through a column of Bio Rad AG 4×4 resin in the formate cycle. The metabolites were eluted from the resin using 60% acetonitrile made 0.2 N with sulfuric acid. Fractions containing the substrate metabolites were put in the freezer for 2–3 hours whereupon two layers formed. The top layer contained essentially all the material of interest. The top layers were drawn off and purified into five fractions by HPLC, using a Zorbax semiprep RX column with a gradient from 42% to 44% acetonitrile in water, containing 0.1% TFA over 20 minutes. The largest peak, eluting at 13 minutes, was further purified using a Zorbax semiprep. CN column, run isocratically with 40% MeCN in water with 0.1% TFA. Fractions of retention time 9.7 minutes were pooled and evaporated to yield 4.2 mE of product.

3. Characterization:

The structure of the novel compound of this invention of formula I was determined by proton NHR spectroscopy. $^1$H NMR (CD$_2$OD) δ: 8:0.85 (d, 3H, 3=6.5 Hz); 0.82 (d, 3H, 3=6.5 Hz); 1.06 (d, 3H, 3=6.5 Hz); 1.09 (d, 3H, 3=6.4 Hz); 1.19–1.55 (m, 3H); 2.03 (m, 2H); 2.24– 2.47 (m, 4H); 2.43 (dd, 2H, 3=14.0 & 8.0 Hz); 2.68 (dd, 2H, J=14.0 & 6.0 Hz); 3.60 (d, 2H, J=6.5 & 4.0 Hz); 4.03 (d, 1H); 4.96 (s, =CH$_2$); 5.02 (s, =CH$_2$); 5.07 (d, 1H, 3=5.0 Hz); 5.30 (s, 1H); 5.80 (d, 1H, J=$\overline{16.0}$ Hz); 6.30 (d, 1H, J=2 Hz); 6.80 (dd, 1H, J=16.0 & 9.0 Hz); 7.14 (t, 1H); 7.18 (d, 1H); 7.24 (t, 1H).

Key observations were the absence of the characteristic terminal methyl triplet and the presence of a novel CH$_3$CH grouping having chemical shifts of 1.09 ppm and 3.60 ppm, respectively. The chemical shift of 3.60 ppm is typical for a CH attached to oxygen. It was reasonable to infer that the structural transformation was confined to the hydroxylation since the chemical shifts of all signals to the left of and including the vinyl protons, as the structure is depicted herein, were virtually coincident with those of the substrate of formula II.

The present invention is also concerned with a method of treating hypercholesterolemia which comprises the administration to a subject in need of such treatment of a nontoxic therapeutically effective amount of a compound represented by structural formula (I) or a pharmaceutically acceptable salt thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but a daily dosage for adults is within a range of from about 20 mg to 2000 mg (preferably 20 to 100 mg) which may be given in two to four divided doses. Higher doses may be favorably employed as required.

The present invention is also concerned with a method of inhibiting squalene synthetase which comprises the administration to a subject in need of such treatment of a nontoxic therapeutically effective amount of a compound represented by structural formula (I) or a pharmaceutically acceptable salt thereof. Specifically, the compounds of this invention are useful in treating disease conditions such as, but not limited to, hypercholesterolemia conditions which require the action of the enzyme squalene synthetase. They may be administered by the same routes in the same dosages as described for the method of treating hypercholesterolemia.

The pharmaceutically acceptable salts of the compounds of this invention include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, or two of the carboxyl groups are in the salt form.

Also included within the scope of this invention are esters of Compound I. The 3, 4 and 5 carbox-/groups of the compound of structural formula (I) may be esterified with the appropriate alkylating agent and DBU. By using 1, 2 or 3 equivalents of the appropriate alkylating agent, Compound I may be selectively esterified. However, esterification may lead to a mixture of mono, di and triesters and these may be separated, by preparative HPLC using a C-8 reverse phase column and a gradient solvent of $H_2O/CH_3CN$. Thus, compounds wherein one or more of the 3, 4 and 5 carboxy groups is esterified are included within this invention. These mono, di and triesters may be selected from $C_{1-5}$ alkyl; $C_{1-5}$ alkyl substituted with a member of the group consisting of phenyl, and phenyl substituted with methyl, methoxy, halogen (Cl, Br, F, I) or hydroxy; or a pharmaceutically acceptable salt of a compound that is a mono or diester.

The compounds of this invention may also be administered in combination with other cholesterol lowering agents such as those which inhibit an enzymatic pathway in the biosynthesis of cholesterol. Example of such agents would include but are not limited to HMG-CoA reductase inhibitors, HMG-COA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibrio acids, clofibrate and gemfibrozil. Appropriate daily dosages for adults are niacin (2–8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastro-intestinal tract. Examples of such polymers include cholestyramine, colestipol and poly[methyl-(3-trimethylaminopropyl)imino-trimethylene dihalide]. The relative amounts of the compounds of this invention and these polymers is between 1:100 and 1:15,000.

The intrinsic squalene synthetase inhibitory activity of the compound of this invention was measured by the ill vitro protocol described below:

PREPARATION OF HUMAN HepG2 cell ENZYME

1. SOURCE: HEPG2 CELL LINE(Liver, hepatoblastoma, Human) ATCC No. HB 8065

2. CELL GROWTH AND MAINTENANCE

Culture Medium: Minimum essential medium (MEM) with non-essential amino acids, sodium pyruvate, and 10% fetal bovine serum. The medium was changed twice weekly. A confluent monolayer was achieved in 1 week. The growth medium is prepared as listed below.

| Solution | Volume (ml) |
| --- | --- |
| 1. MEM (Gibco #320-1090AK) With Earle's salts and L-glutamine | 1000 |
| 2. Penicillin (10,000 units/ml), streptomycin (10,000 mg/ml), Gibco #600-5140 PG | 10 |
| 3. MEM sodium pyruvate, 10 mM (100X) Gibco #320-1140 | 10 |
| 4. MEM nonessential amino acids, 10 mM (100X) Gibco #320-1140AG | 10 |
| 5. L-glutamine, 200 mM (100X), Gibco #320-5030AG | 10 |
| 6. Hyclone fetal bovine serum, defined, Hyclone #A-111-L | 100 |

Subculture Procedure: Remove medium, wash with PBS, add fresh trypsin (0.25%)-EDTA (0.02%) with Hank's Balanced Salt solution and let flask stand for a minute and remove the trypsin solution. Incubate flask at 37° C. until cells detached. Add fresh medium, disperse and dispense cells into new flasks. Subcultivation ratio: 1:6.

PREPARATION of Delipidated Serum: Fetal calf serum(100 ml) and CAB-O-Sil (2 grams) stir overnight at 4° C. and centrifuge at 16,000 rpm for 5 hrs. Filter supernatant and store at 4° C.

48 hrs. prior to harvest, switch cells grown in MEM with 10% Fetal Calf serum to HEM with 10% delipidated serum.

3. Harvest: Remove medium, wash with PBS, add fresh trypsin (0.25%)-EDTA (0.02%) with Hank's Balanced Salt solution, rinse and remove. Incubate flask at 37° C. until cells detach. Add 6 ml of MEM medium per flask to suspend cells and combine into centrifuge tube. Spin cells at 1,000 rpm for 5 mins. Wash by resuspending cell pellet in PBS and repeat centrifuging. Count cells (2.5×109 yield from 18 flasks (75 $cm^2$). Resuspend in 10 mls of 50 mM HEPES (N-[2-Hydroxyethyl]piperazine-N'-[2-ethanesulfonic acid]) containing 5 mM $MgCl_2$, 2 mM $MnCl_2$, 10 mM DTT, pH 7.5 (enzyme suspension buffer).

4. Cell extracts: Sonicate (probe sonicator setting *190 60, pulse) the cell suspension on ice for 2 min. After a 1 min. cooling on ice, the sonication is repeated until greater than 90% of the cells are broken as observed microscopically. Centrifuge cell suspension for 10 mins. at 10,000 rpm. Transfer supernatant to clean tube and centrifuge at 20,000 rpm for 20 mins. The HepG2 enzyme preparation was centrifuged at 34,000 rpm to separate the cytosol and microsomal enzymes. The resulting pellet from the 34,000 rpm centrifugation, containing the equals the synthetase, was resuspended in 5 ml of enzyme suspension buffer. The enzyme suspension was diluted 1 to 1,536 and used to perform the squalene synthetase assay using 3 µM $^3$H-farnesyl pyrophosphate as the substrate.

SQUALENE SYNTHETASE ASSAY

Reactions were performed in 1.2 ml polypropylene tube strips of 8. Buffer mixture and substrate mixture for the assay were prepared from the following solution:

Buffer mixture contains 270 mM HEPES, pH 7.5, 20 mM

Potassium fluoride and 5.4 mM Dithiothreitol(DTT). 55 gl of this mixture was used per assay. The final concentrations of HEPES, KF and DTT in the assay are 150 mM, 11 mM and 3 mM respectively.

| | Substrate mixture: | | |
|---|---|---|---|
| | Stock concentration | μl used per assay | Final concentration |
| 1. | $MgCl_2$, 55 mM | 10 | .5 mM |
| 2. | NADPH, 10 mM (made fresh) | 10 | 1 Mm |
| 3. | $^3$H-farnesyl-pyrophosphate, 25 μM, 20 Ci per mole | 0.24 | 0.06 μM |
| 4. | Farnesyl-pyrophosphate, 3 mM | 0.098 | 2.94 μM |
| 5. | Water | 9.65 | |

For each reaction, 55 μl of buffer mixture was taken with 5 μl of an inhibitor solution in MeOH and 10 μl of diluted enzyme (1 to 1536 as described in the enzyme preparation, the final protein concentration of enzyme in the assay is 1.2 μg per ml.). The reaction was initiated by the addition of 30 μl of substrate solution and the mixture was incubated at 30° C. for 20 minutes. The reactions were stopped by the addition of 100 μl of 95 % EtOH, 10 vortexed, and 100 μl of a suspension of 1 gram per ml of Bio-Rad AG 1×8 resin(400 mesh, Chloride form) was then added, vortexed. 800 μl of heptane was added to each tube strip and the strips were capped and vortexed for 10 minutes. 400 μl of heptane layer was then removed into a minimal and mixed with 2.5 ml of scintillation fluid and the radioactivity was determined by liquid scintillation counting. The controls were run with 5 μl of MeOH and blanks were run with the addition of 100 μl of 95% EtOH to denature the enzyme before the addition of the substrate mixture to the assay tube.

Percent inhibition is calculated by the formula:

$$\frac{(\text{Control} - \text{Sample}) \times 100}{\text{Control} - \text{Blank}}$$

$IC_{50}$ values were determined by plotting the log of the concentration of the test compound versus the percentage inhibition. The $IC_{50}$ is the concentration of inhibitor that gives 50% inhibition as determined from these plots. The $IC_{50}$ of the compound of this invention against squalene synthetase is estimated to be 0.091 nM with a dose related inhibition. The compound of this invention inhibits 99% of the squalene synthetase activity when tested at a concentration of 1.8 nM.

EXAMPLE 2

Preparation of the 3,4,5-trimethyl ester of Compound (I)

A solution of 2 mg of Compound (I) in 0.5 ml of acetonitrile is treated at room temperature with 10 equivalents of DBU and 10 equivalents of methyl iodide. After 2 hours, the reaction is diluted with 10 ml of dichloromethane and washed successively with 10 ml of 0.1 M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give the trimethyl ester of Compound (I).

The method of Example 2 is also suitable for the preparation of other ester derivatives such as 1) ethyl and other lower alkyl esters and 2) benzyl and substituted benzyl esters.

What is claimed is:

1. A compound of structure:

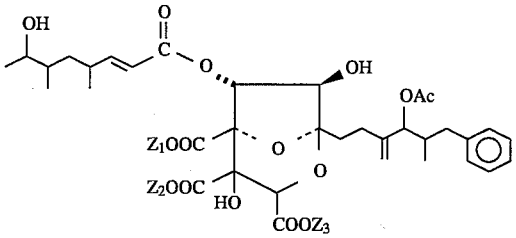

wherein $Z_1$, $Z_2$ and $Z_3$ are each independently selected from the group consisting of (a) B;

(b) $C_{1-5}$ alkyl;

(c) $C_{1-5}$ alkyl substituted with a member of the group consisting of (i) phenyl, (ii) phenyl substituted with methyl, methoxy, halogen (Cl, Br, I, F), or hydroxy; or a pharmaceutically acceptable salt thereof.

2. A compound of claim 1 wherein $Z_1$, $Z_2$ and $Z_3$ are each hydrogen.

3. A pharmaceutical antihypercholesterolemic composition comprising a pharmaceutically acceptable carrier and a therapeutically effective amount of the compound of claim 1.

4. A method of treatment of hypercholesterolemia comprising the administration to a subject in need of such treatment of a therapeutically effective amount of the compound of claim 1.

5. A method of inhibiting squalene synthetase comprising the administration to a subject in need of such treatment of a therapeutically effective amount of the compound of claim 1.

* * * * *